US006861245B1

(12) United States Patent
Smit

(10) Patent No.: US 6,861,245 B1
(45) Date of Patent: Mar. 1, 2005

(54) PRODUCTION OF HETEROLOGOUS POLYPEPTIDES FROM FRESHWATER CAULOBACTER

(75) Inventor: John Smit, Richmond (CA)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/913,414

(22) PCT Filed: Feb. 21, 2000

(86) PCT No.: PCT/CA00/00173

§ 371 (c)(1),
(2), (4) Date: Dec. 6, 2001

(87) PCT Pub. No.: WO00/49163

PCT Pub. Date: Aug. 24, 2000

(30) Foreign Application Priority Data

Feb. 19, 1999 (CA) .............................. 2261186

(51) Int. Cl.$^7$ ................................. C12N 1/20
(52) U.S. Cl. .................................... 435/252.3
(58) Field of Search ............................ 435/69.1, 252.3, 435/320.1, 69.7, 70.14, 325; 530/350; 536/23.4

(56) References Cited

U.S. PATENT DOCUMENTS

| 5,143,830 A | 9/1992 | Holland et al. |
| 5,500,353 A | 3/1996 | Smit et al. |
| 5,976,864 A | 11/1999 | Smit et al. |
| 6,210,948 B1 | 4/2001 | Smit et al. |

FOREIGN PATENT DOCUMENTS

| CA | 2090549 | 12/1993 |
| WO | WO 95/19371 | 7/1995 |
| WO | WO 00/49163 | 8/2000 |

OTHER PUBLICATIONS

Awram P, Smit J. The Caulobacter crescentus paracrystalline S–layer protein is secreted by an ABC transporter (type I) secretion apparatus. J Bacteriol. 1998 Jun.;180(12):3062–9.*
Alley et al., (1991) Genetics 129:333–341.
Altschul et al., (1990) J. Mol. Biol. 215:403–410.
Ausubel et al., (1994) *Current Protocols in Molecular Biology*, John Wiley & Sons, Inc., New York, 16.4.1–16.4.17 Supplement 28.
Bagdasarian et al., (1981) Gene 16:237–247.
Barry, G. F., (1988) Gene 71:75–84.
Beveridge et al., Summary Statements in *Advances in Bacterial Paracrystalline Surface Layers* Beveridge and Koval eds. Plenum Press Chapter 37: 323–327.
Bingle et al., (1990) Plasmid 24:143–148.
Bingle et al., (1991) Biotechniques 10:150–152.
Bingle et al., (1992) BioforBioqual '92, Vancouver, Canada, Jun. 9–11, 1992.
Bingle et al., (1993) Can. J. Microbiol. 39:70–80.
Bingle et al., (1993), Definition of Form and Function for the S–Layer of Caulobacter crecentus in *Advances in Bacterial Paracrystalline Surface Layers* Beveridge and Koval eds. Plenum Press Chapter 18:181–193.
Bingle et al., (1993), Linker Mutagenesis of the Caulobacter crecentus S–Layer Protein in *Advances in Bacterial Paracrystalline Surface Layers* Beveridge and Koval eds. Plenum Press Chapter 30:293–296.
Bingle et al., (1994) Can. J. Microbiol. 40:777–782.
Bingle et al., (1996) Can. J. Microbiol. 42(7):672–684.
Bingle et al., (1997) Molecular Microbiology 26(2):277–288.
Bingle et al., (1997) J. Bacteriol. 179(3):601–611.
Burnette, (1981) Analytical Biochemistry 112:195–203.
Charbit et al., (1988) Gene 70:181–189.
Edwards et al., (1991) J. Bacteriol. 193:5568–5572.
Engleberg et al., (1984) Infection and Immunity 44:222–227.
Fellay et al., (1987) Gene 52:147–154.
Fisher et al., (1988) J. Bacteriol. 170:4706–4713.
Gilchrist et al., (1991) J. Bacteriol. 173:921–925.
Gilchrist et al., (1992) Can. J. Microbiol. 38:193–202.
Hayes et al., (1991) J. General Micorbiology 137:1557–1564.
Hynes et al., (1989) Gene 78:111–119.
Hoffman et al., (1985) Proc. Natl. Acad. Sci. U.S.A. 82:5107–5111.
Koener et al., (1987) Journal of Virology 61:1342–1349.
Kovach et al., (1994) BioTechniques 16:800–802.
Landon, (1977) Methods in Enzymology vol. XLVII No. part E:145–149.
Leong (1993) Curr. Opini. Biotech. 4:286–293.
Macrae et al., (1991) Applied and Enviormental Microbiology 57:751–758.
Nomellini et al., (1995) Abstracts of the General Meeting of the American Society for Microbiology vol. 95:525.
Pugsley, (1991) Superfamilies of bacterial transport systems with nucleotide binding components. In *Prokaryotic Structure and Function: A New Perspective.* Mohan et al. eds. Cambridge University Press, New York at pp. 224–248.
Pugsley, (1993) Microbiol. Rev. 57:50–108.

(List continued on next page.)

*Primary Examiner*—Karen Cochrane Carlson
*Assistant Examiner*—Sheridan Snedden
(74) *Attorney, Agent, or Firm*—Scully, Scott, Murphy & Presser

(57) ABSTRACT

A method is provided for screening *Caulobacter* suitable for use as host organisms for secretion of heterologous polypeptides. Such *Caulobacter* have a transport protein homologous to one of the type I transport proteins known in *C. crescentus*. DNA constructs are also provided which code for a chimeric protein of which the C-terminus is a secretion signal of a *Caulobacter* surface layer protein, other than from *C. crescentus*. Bacterial cells containing, or which express such DNA constructs and which may secrete the resulting protein, are also provided.

20 Claims, 1 Drawing Sheet

OTHER PUBLICATIONS

Smit, (1995) Annual Meeting of the American Society for Microbiology–Poster Presentation, Washington D.C., May 24, 1995.

Smit et al., (1991) Use of Caulobacters to Separate Toxic Heavy Metals from Wastewater Streams, Apr. 1991 US Department of Energy Publication.

Smit et al., (1991) Use of Caulobacters to Separate Toxic Heavy Metals from Wastewater Streams in *Proceedings of Waste Stream Management & Utilization Innovative Concepts—An Experimental Technique Exchange vol. 1 Mining & Metals Remediation,* Wash. D.C. Apr. 25–26, 1991, US Department of Energy, Pacific Northwest Lab, Richland Washington; at pp. 6.1–6.11.

*Federal Grant is First for Manmade Cleanup Bug,* in Environment Today vol. 2 Nov./Dec. 1991.

Smit, (1986) "Protein Surface Layers of Bacteria", in *Outer Membranes as Model System,* Inouye M. Ed. J. Wiley & Sons, at p. 343–376.

Smit et al., (1984) J. Bacteriol. 160:1137–1145.

Smit et al., (1981) J. of Biol. Chem. 256:3092–3097.

Stahl et al., (1992) J. Bacteriol. 174:2193–2198.

Tijssen, (1993), *Laboratory Techniques in Biochemistry and Molecular Biology—Hybridization with Nucleic Acid Probes,* Part I, Chapter 2 "Overview of Principles of Hybridization and the Strategy of Nucleic Acid Probe Assays", Elsevier, New York.

Vieira et al., (1982) Gene 19:259–268.

Walker et al., (1992) J. Bacteriol. 174:1783–1792.

Xu et al., (1991) Journal of Virology 65:1611–1615.

\* cited by examiner

SEQUENCE LISTING

<160> NUMBER OF SEQ ID NOS: 7

<210> SEQ ID NO 1
<211> LENGTH: 82
<212> TYPE: PRT
<213> ORGANISM: Caulobacter crescentus

<400> SEQUENCE: 1

Ala Phe Gly Ala Ala Val Thr Leu Gly Ala Ala Thr Leu Ala Gln
1               5                   10                  15

Tyr Leu Asp Ala Ala Ala Gly Asp Gly Ser Gly Thr Ser Val Ala
                20                  25                  30

Lys Trp Phe Gln Phe Gly Gly Asp Thr Tyr Val Val Asp Ser Ser
            35                  40                  45

Ala Gly Ala Thr Phe Val Ser Gly Ala Asp Ala Val Ile Lys Leu Thr
        50                  55                  60

Gly Leu Val Thr Leu Thr Thr Ser Ala Phe Ala Thr Glu Val Leu Thr
65                  70                  75                  80

Leu Ala

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
cggaatcgcg ctacgcgctg g                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer -continued

<400> SEQUENCE: 3
gggagctcga agggtcctga                                                                                    20

<210> SEQ ID NO 4
<211> LENGTH: 555
<212> TYPE: PRT
<213> ORGANISM: Caulobacter crescentus

<400> SEQUENCE: 4

```
Met Phe Lys Arg Ser Gly Ala Lys Pro Thr Ile Phe Asp Gln Ala Val
 1               5                  10                  15

Leu Val Ala Arg Pro Ala Val Ile Thr Ala Met Val Phe Ser Phe Phe
            20                  25                  30

Ile Asn Ile Leu Ala Leu Val Ser Pro Leu Tyr Met Leu Gln Val Tyr
        35                  40                  45

Asp Arg Val Leu Thr Ser Arg Asn Val Ser Thr Leu Ile Val Leu Thr
    50                  55                  60

Val Ile Cys Val Phe Leu Phe Leu Val Tyr Gly Leu Leu Glu Ala Leu
65                  70                  75                  80

Arg Thr Gln Val Leu Val Arg Gly Gly Leu Lys Phe Asp Gly Val Ala
                85                  90                  95

Arg Asp Pro Ile Phe Lys Ser Val Leu Asp Ser Thr Leu Ser Arg Lys
           100                 105                 110

Gly Ile Gly Gly Gln Ala Phe Arg Asp Met Asp Gln Val Arg Glu Phe
       115                 120                 125

Met Thr Gly Gly Leu Ile Ala Phe Cys Asp Ala Pro Trp Thr Pro Val
   130                 135                 140

Phe Val Ile Val Ser Trp Met Leu His Pro Phe Phe Gly Ile Leu Ala
145                 150                 155                 160

Ile Ile Ala Cys Ile Ile Ile Phe Gly Leu Ala Val Met Asn Asp Asn
                165                 170                 175

Ala Thr Lys Asn Pro Ile Gln Met Ala Thr Met Ala Ser Ile Ala Ala
           180                 185                 190

Gln Asn Asp Ala Gly Ser Thr Leu Arg Asn Ala Glu Val Met Lys Ala
       195                 200                 205

Met Gly Met Trp Gly Gly Leu Gln Ala Arg Trp Arg Ala Arg Arg Asp
   210                 215                 220

Glu Gln Val Ala Trp Gln Ala Ala Ser Asp Ala Gly Gly Ala Val
225                 230                 235                 240

Met Ser Gly Ile Lys Val Phe Arg Asn Ile Val Gln Thr Leu Ile Leu
                245                 250                 255

Gly Gly Gly Ala Tyr Leu Ala Ile Asp Gly Lys Ile Ser Ala Gly Ala
           260                 265                 270

Met Ile Ala Gly Ser Ile Leu Val Gly Arg Ala Leu Ala Pro Ile Glu
       275                 280                 285

Gly Ala Val Gly Gln Trp Lys Asn Tyr Ile Gly Ala Arg Gly Ala Trp
   290                 295                 300

Asp Arg Leu Gln Thr Met Leu Arg Glu Glu Lys Ser Ala Asp Asp His
305                 310                 315                 320

Met Pro Leu Pro Glu Pro Arg Gly Val Leu Ser Ala Glu Ala Ala Ser
                325                 330                 335

Ile Leu Pro Pro Gly Ala Gln Gln Pro Thr Met Arg Gln Ala Ser Phe
           340                 345                 350

Arg Ile Asp Ala Gly Ala Ala Val Ala Leu Val Gly Pro Ser Ala Ala
```

-continued

```
             355                 360                 365
Gly Lys Ser Ser Leu Leu Arg Gly Ile Val Gly Val Trp Pro Cys Ala
    370                 375                 380

Ala Gly Val Ile Arg Leu Asp Gly Tyr Asp Ile Lys Gln Trp Asp Pro
385                 390                 395                 400

Glu Lys Leu Gly Arg His Val Gly Tyr Leu Pro Gln Asp Ile Glu Leu
                405                 410                 415

Phe Ser Gly Thr Val Ala Gln Asn Ile Ala Arg Phe Thr Glu Phe Glu
            420                 425                 430

Ser Gln Glu Val Ile Glu Ala Ala Thr Leu Ala Gly Val His Glu Met
        435                 440                 445

Ile Gln Ser Leu Pro Met Gly Tyr Asp Thr Ala Ile Gly Glu Gly Gly
    450                 455                 460

Ala Ser Leu Ser Gly Gly Gln Arg Gln Arg Leu Ala Leu Ala Arg Ala
465                 470                 475                 480

Val Phe Arg Met Pro Ala Leu Leu Val Leu Asp Glu Pro Asn Ala Ser
                485                 490                 495

Leu Asp Gln Val Gly Glu Val Ala Leu Met Glu Ala Met Lys Arg Leu
            500                 505                 510

Lys Ala Ala Lys Arg Thr Val Ile Phe Ala Thr His Lys Val Asn Leu
        515                 520                 525

Leu Ala Gln Ala Asp Tyr Ile Met Val Ile Asn Gln Gly Val Ile Ser
    530                 535                 540

Asp Phe Gly Glu Arg Asp Arg Cys Trp Pro Ser
545                 550                 555

<210> SEQ ID NO 5
<211> LENGTH: 435
<212> TYPE: PRT
<213> ORGANISM: Caulobacter crescentus

<400> SEQUENCE: 5

Met Lys Pro Pro Lys Ile Gln Arg Pro Thr Asp Asn Phe Gln Ala Val
1               5                   10                  15

Ala Arg Ile Gly Tyr Gly Ile Ile Ala Leu Thr Phe Val Gly Leu Leu
            20                  25                  30

Gly Trp Ala Ala Phe Ala Pro Leu Asp Ser Ala Val Ile Ala Asn Gly
        35                  40                  45

Val Val Ser Ala Glu Val Ser Gln Asp Val Gln His Leu Glu Gly Gly
    50                  55                  60

Met Leu Ala Lys Ile Leu Val Arg Glu Gly Glu Lys Val Lys Ala Gly
65                  70                  75                  80

Gln Val Leu Phe Glu Leu Asp Pro Thr Gln Ala Asn Ala Ala Ala Gly
                85                  90                  95

Ile Thr Arg Asn Gln Tyr Val Ala Leu Lys Ala Met Glu Ala Arg Leu
            100                 105                 110

Leu Ala Glu Arg Asp Gln Arg Pro Ser Ile Ser Phe Pro Ala Asp Leu
        115                 120                 125

Thr Ser Gln Arg Ala Asp Pro Met Val Ala Arg Ala Ile Ala Asp Glu
    130                 135                 140

Gln Ala Gln Phe Thr Glu Arg Arg Gln Thr Ile Gln Gly Gln Val Asp
145                 150                 155                 160

Leu Met Asn Ala Gln Arg Leu Gln Tyr Gln Ser Glu Ile Glu Gly Ile
                165                 170                 175
```

-continued

```
Asp Arg Gln Thr Gln Gly Leu Lys Asp Gln Leu Gly Phe Ile Glu Asp
            180                 185                 190

Glu Leu Ile Asp Leu Arg Lys Leu Tyr Asp Lys Gly Leu Val Pro Arg
        195                 200                 205

Pro Arg Leu Leu Ala Leu Glu Ala Arg Ala Gly Ser Leu Ser Gly Ser
    210                 215                 220

Ile Gly Arg Leu Thr Ala Asp Arg Ser Lys Ala Val Gln Gly Ala Ser
225                 230                 235                 240

Asp Thr Gln Leu Lys Val Arg Gln Ile Lys Gln Glu Phe Phe Glu Gln
                245                 250                 255

Val Ser Gln Ser Ile Thr Glu Thr Arg Val Arg Leu Ala Glu Val Thr
            260                 265                 270

Glu Lys Glu Val Val Ala Ser Asp Ala Gln Lys Arg Ile Lys Ile Val
        275                 280                 285

Ser Pro Val Asn Gly Thr Ala Gln Asn Leu Arg Phe Phe Thr Glu Gly
    290                 295                 300

Ala Val Val Arg Ala Ala Glu Pro Leu Val Asp Ile Ala Pro Glu Asp
305                 310                 315                 320

Glu Ala Phe Val Ile Gln Ala His Phe Gln Pro Thr Asp Val Asp Asn
                325                 330                 335

Val His Met Gly Met Val Thr Glu Val Arg Leu Pro Ala Phe His Ser
            340                 345                 350

Ala Gly Asn Pro Asp Pro Glu Arg His Asp Pro Val Ala Val Ala Asp
        355                 360                 365

Arg Ile Ser Asp Pro Gln Lys Gln Ala Arg Leu Phe Leu Gly Ile Val
    370                 375                 380

Arg Val Asp Val Lys Gln Leu Pro Pro His Leu Arg Gly Arg Val Thr
385                 390                 395                 400

Ala Gly Met Pro Ala Gln Val Ile Val Pro Thr Gly Glu Arg Thr Val
                405                 410                 415

Leu Gln Tyr Leu Phe Ser Pro Leu Arg Asp Thr Leu Arg Thr Thr Met
            420                 425                 430

Arg Glu Glu
        435
```

```
<210> SEQ ID NO 6
<211> LENGTH: 100
<212> TYPE: PRT
<213> ORGANISM: Caulobacter sp. FWC1

<400> SEQUENCE: 6

Thr Thr Asp Thr Leu Lys Phe Ala Asn Thr Gly Thr Glu Thr Phe Thr
1               5                   10                  15

Ser Thr Lys Val Asp Leu Thr Gly Val Asn Asp Phe Thr Ala Ala Leu
            20                  25                  30

Asn Ala Ala Ala Gly Asn Gly Gly Asn Gly Ile Ile Thr Trp
        35                  40                  45

Phe Gln Tyr Gly Gly Asn Thr Tyr Ile Val Glu Asp Arg Asp Ala Gly
    50                  55                  60

Asn Thr Phe Asn Val Ala Thr Asp Ile Val Lys Leu Thr Gly Ala
65                  70                  75                  80

Val Asp Leu Ser Thr Ala Val Leu Ser Ala Phe Gly Arg Arg Ser Ser
                85                  90                  95

Leu Thr Leu Val
        100
```

```
<210> SEQ ID NO 7
<211> LENGTH: 100
<212> TYPE: PRT
<213> ORGANISM: Caulobacter sp. FWC19

<400> SEQUENCE: 7

Arg Ala His Met Ile Leu Lys Pro Thr Arg His Val Ser Asp Arg Trp
 1               5                  10                  15

Gly Arg His Val Ala Arg Leu Val Gln Leu Pro Gly Arg Pro Cys Pro
            20                  25                  30

Lys Leu Ser Asp Ala Ala Thr Thr Gly Asn Ala Ser His Lys Val Ser
        35                  40                  45

Trp Phe Val Tyr Gly Gly Asp Thr Tyr Leu Val Lys Met Ser Thr Leu
    50                  55                  60

Ala Pro Pro Ser Lys Thr Ala Arg Thr Ile Val Val Lys Leu Thr Gly
65                  70                  75                  80

Thr Thr Asn Asp Leu Thr Lys Ala Thr Phe Asp Gly Ala Ala His Thr
                85                  90                  95

Leu Thr Leu Gly
            100
```

PRODUCTION OF HETEROLOGOUS POLYPEPTIDES FROM FRESHWATER CAULOBACTER

FIELD OF INVENTION

This invention relates to the use of the *Caulobacter* surface layer protein (S-layer protein) transport system for the expression and secretion of heterologous polypeptides from a host organism.

BACKGROUND OF THE INVENTION

Many genera of bacteria assemble layers composed of repetitive, regularly aligned, proteinaceous sub-units on the outer surface of the cell. These layers are essentially two-dimensional paracrystalline arrays, and being the outer molecular layer of the organism, directly interface with the environment. Such layers are commonly known as S-layers and are found on members of every taxonomic group of walled bacteria including: *Archaebacteria; Chlamydia; Cyanobacteria; Acinetobacter; Bacillus; Aquaspirillum; Caulobacter; Clostridium; Chromatium*. Typically, an S-layer will be composed of an intricate, geometric array of at least one major protein having a repetitive regular structure. In many cases, such as in *Caulobacter*, the S-layer protein is synthesized by the cell in large quantities and the S-layer completely envelopes the cell and thus appears to be a protective layer.

*Caulobacter* are natural inhabitants of most soil and freshwater environments and may persist in waste water treatment systems and effluents. The bacteria alternate between a stalked cell that is attached to a surface, and an adhesive motile dispersal cell that searches to find a new surface upon which to stick and convert to a stalked cell. The bacteria attach tenaciously to nearly all surfaces and do so without producing the extracellular enzymes or polysaccharide "slimes" that are characteristic of most other surface attached bacteria. They have simple requirements for growth. The organism is ubiquitous in the environment and has been isolated from oligotrophic to mesotrophic situations. *Caulobacters* are known for their ability to tolerate low nutrient level stresses, for example, low phosphate levels. This nutrient can be limiting in many leachate waste streams, especially those with high levels of iron or calcium.

Freshwater *Caulobacter* producing S-layers may be readily detected by negative stain transmission electron microscopy techniques. *Caulobacter* may be isolated using the methods outlined by MacRae, J. D. and Smit (1991) Applied and Environmental Microbiology 57:751–758, which take advantage of the fact that *Caulobacter* can tolerate periods of starvation while other soil and water bacteria may not and that they all produce a distinctive stalk structure, visible by light microscopy (using either phase contrast or standard dye staining methods). Once *Caulobacter* strains are isolated in a typical procedure, colonies pended 2% ammonium molybdate negative stain and applied to plastic-filmed, carbon-stabilized 300 or 400 mesh copper or nickel grids and examined in a transmission electron microscope at 60 kilovolt accelerating voltage, as described in Smit, J. (1986) "Protein Surface Layers of Bacteria", in *Outer Membranes as Model System*, M. Inouge, Ed. J. Wiley & Sons, at page 343–376. S-layers are seen a two-dimensional geometric patterns most readily on those cells in a colony that have lysed and released their internal contents.

The S-layer of different freshwater *Caulobacter* is hexagonally arranged with a similar centre—centre dimension and antisera raised against the S-layer protein of *C. crescentus* strain CB15 reacts with S-layer proteins from other *Caulobacter* (see: Walker, S. G., et al. (1992) (J. Bacteriol. 174:1783–1792). All S-layer proteins isolated from *Caulobacter* may be substantially purified using the same extraction method (pH extraction). All strains appear to have a lipopolysaccharide (LPS) reactive with antisera against the CB15 strain lipopolysaccharide species. The LPS appears to be required for S-layer attachment.

The S-layer elaborated by freshwater isolates of *Caulobacter* are visibly indistinguishable from the S-layer produced by *Caulobacter crescentus* strains CB2 and CB15. The S-layer proteins from the latter strains have approximately 100.000 m.w. although sizes of S-layer proteins from other species and strains will vary. The protein has been characterized both structurally and chemically. It is composed of ring-like structures spaced at 22 nm intervals arranged in a hexagonal manner on the outer membrane. The S-layer is bound to the bacterial surface and may be removed by low pH treatment or by treatment with a calcium chelator such as EDTA.

The similarity of S-layer proteins in different strains of *Caulobacter* permits the use of a cloned S-layer protein gene of one *Caulobacter* strain for retrieval of the corresponding gene in other *Caulobacter* strains (see: Walker, S. G. et al. (1992) [supra]: and, MacRae, J. D. et al. (1991) [supra].

Expression, secretion and optionally, presentation of a heterologous polypeptide in *Caulobacter* provides advantages not previously seen in systems using organisms such as *E. coli* and *Salmonella* in which fusion products using different surface proteins have been reported. All known *Caulobacter* strains are believed to be harmless and are nearly ubiquitous in aquatic environments. In contrast, many *Salmonella* and *E. coli* strains are pathogens. Consequently, expression and secretion of a heterologous polypeptide using *Caulobacter* as a vehicle will have the advantage that the expression system will be stable in a variety of outdoor environments and may not present problems associated with the use of a pathogenic organism. Furthermore, *Caulobacter* are natural biofilm forming species and may be adapted for use in fixed biofilm bioreactors. The quantity of S-layer protein that is synthesized and is secreted by *Caulobacter* is high, reaching 12% of the cell protein. The unique characteristics of the repetitive, two-dimensional S-layer would also make such bacteria ideal for use as an expression system, or as a presentation surface for heterologous polypeptides. This is desirable in a live vaccine to maximize presentation of the antigen or antigenic epitope. In addition, use of such a presentation surface to achieve maximal exposure of a desired polypeptide to the environment results in such bacteria being particularly suited for use in bioreactors or as carriers for the polypeptide in aqueous or terrestrial outdoor environments.

The invention described in the PCT application published Sep. 18, 1997 under WO 97/34000 describes the C-terminal region of *Caulobacter crescents* S-layer protein as being essential for secretion of S-layer protein in that species. Heterologous polypeptides may be conveniently expressed and secreted by a host *Caulobacter* when the polypeptide is expressed as a fusion with the C-terminal secretion signal. Further studies with *C. crescentus* have demonstrated that the species employs a type I secretion system which involves an uncleaved C-terminal secretion signal on the surface layer protein (RsaA) and several transport proteins encoded by genes 3' to the surface layer protein gene (rsaA) (Amram, P. and Smit, J. (1998) Journal of Bacteriology 180:3062–3069).

A typical type I secretion system uses three transport protein components. One such component, the ABC transporter, is embedded in the inner membrane, contains an ATP-binding region, recognizes the C-terminal secretion signal of the substrate protein, and hydrolyzes ATP during the transport process. Another component, the membrane fusion protein (MFP) is anchored in the inner membrane and appears to span the periplasm. The remaining component is an outer membrane protein (OMP) that is thought to interact with the MFP to form a channel that extends from the cytoplasm through the two membranes to the outside of the cell. In *C. crescentus*, the ABC transporter and the MFP proteins have been termed RsaD and RsaE (respectively) and their genes are immediately 3' of rsaA. Further downstream is the rsaF gene which is believed to encode the OMP.

It is desirable to provide for the use of *Caulobacter* species other than *C. crescentus* in the expression and secretion of heterologous polypeptides from a host organism.

SUMMARY OF INVENTION

This invention is based on the discovery that S-layer producing freshwater *Caulobacter* (other than *C. crescentus*) rely on a type I secretion signal located at the C-terminus of the S-layer protein and highly conserved transport proteins. While the secretion signal itself is not as well conserved as the transport proteins, a secretion signal from a first species of *Caulobacter* will be recognized by the transport mechanism of other species. Thus, a surface layer protein secretion signal derived from any freshwater S-layer producing *Caulobacter* may be used in the invention described in WO 97/34000. As well, any *Caulobacter* which contains a type I secretion system may be used as a host organism for the expression and secretion of heterologous polypeptides to which a *Caulobacter* S-layer protein secretion signal has been fused. Nucleic acid constructs made for expression of heterologous polypeptides may include a surface layer protein secretion signal from a *Caulobacter* other than *C. crescentus*, for expression in the same species from which the surface layer protein signal was derived or for expression in a different species. Furthermore, a C-terminal secretion signal derived from the S-layer protein (RsaA) of *C. crescentus*, may be used in such transformation of *Caulobacter* other than *C. crescentus*.

This invention also provides the use of *Caulobacter* other than *C. crescentus* as a host organism for the expression of polypeptides heterologous to a surface layer protein of the *Caulobacter*, wherein the *Caulobacter* has at least one surface layer transport protein that is homologous to RsaD or RsaE of *C. crescentus*. This invention also provides a method for identifying a candidate *Caulobacter* for such use, comprising extracting DNA from the *Caulobacter*, contacting the DNA with an oligonucleotide that is selectively hybridizable to one of rsaD and rsaE of *C. crescentus*, and determining whether the oligonucleotide hybridizes to the DNA. The sequences of RsaD and RsaE and coding sequences rsaD and rsaE are known.

This invention also provides a *Caulobacter* host, wherein the host comprises at least one surface layer transport protein having an amino acid sequence homologous to RsaD or RsaE, and wherein the host further comprises a DNA construct for expression of a polypeptide heterologous to a surface layer protein of the host, the construct comprising DNA encoding a heterologous polypeptide 5' to and operably linked with DNA encoding a *Caulobacter* surface layer protein secretion signal, with the proviso that when the host comprises transport proteins having sequences the same as both RsaD and RsaE, the secretion signal is not from *C. crescentus*.

This invention also provides a DNA construct comprising one or more restriction sites for facilitating insertion of DNA into the construct, wherein the construct further comprises DNA encoding a *Caulobacter* surface layer protein secretion signal not present in *C. crescentus*.

This invention also provides a DNA construct for expression of a heterologous polypeptide comprising DNA encoding a polypeptide not present in *Caulobacter* surface layer protein 5' from and operatively linked to DNA encoding a surface layer protein secretion signal not present in *C. crescentus*.

A surface layer protein secretion signal not present in *C. crescentus* will function as such a signal in a *Caulobacter* type I secretion system but will not have an amino acid sequence that is the same as amino acids 945–1026 of the Rsa protein of *C. crescentus*. The latter sequence (SEQ ID NO:1) is:
AFGAAVTLGAAATLAQYLDAAAAGDGSGTSVAKW-
FQFGGDTYVVVDSSAGATFVSGADAVIKLT-
GLVTLTTSAFATEVLTLA This invention also provides a bacterial cell comprising the aforementioned DNA constructs. Where the bacterial cell is other than *C. crescentus*, the DNA construct may comprise a surface layer protein secretion signal derived from RsaA. This invention also provides the use of the aforementioned DNA constructs for transformation of bacterial cells and the use of such cells for expression and secretion of polypeptides heterologous to the cell. Where the cell is *Caulobacter*, the polypeptide is heterologous to the S-layer protein of the cell. This invention also provides proteins comprising heterologous material, secreted from a *Caulobacter* in which the secretion signal is not found in *C. crescentus*.

DESCRIPTION OF THE DRAWINGS

For better understanding of this invention, reference may be made to the preferred embodiments and examples described below, and the accompanying drawing in which.

DESCRIPTION OF THE PREFERRED EMBODIMENTS

Figure 1:
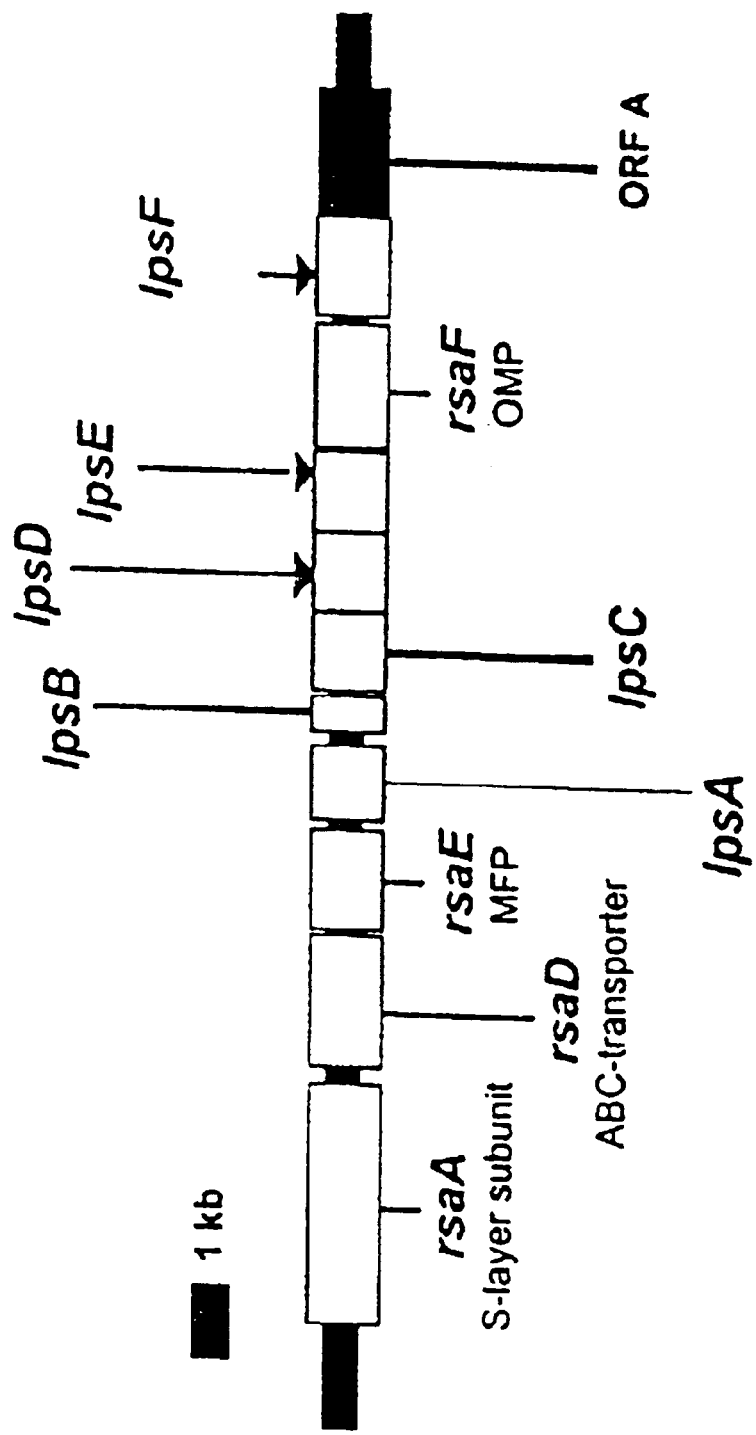
FIG. 1 shows the organization of the *C. crescentus* genome with respect to the surface layer protein subunit gene (rsaA) and the downstream (3') type I transport protein genes: rsaD (encodes the ABC-transporter), rsaE (encodes the membrane fusion protein (MPF) and rsaF (encodes the outer membrane protein OMP). LPS genes A–F are involved in the production of lipopolysaccharides.

Organisms for use in this invention include all S-layer producing freshwater species or strains of *Caulobacter*. While similarity of the S-layer gene and S-layer secretion systems permits the use of different S-layer protein producing freshwater *Caulobacter* in this invention, the C-terminal secretion signals of the S-layer genes of *C. crescentus* strains CB2 and CB15 (and variants of those strains which contain homologs of the rsaA gene encoding the 1026 amino acid paracrystalline S-layer protein described in: Gilchrist, A. et al. 1992 Can. J. Microbiol. 38:193–208) are specifically referred to in the detailed description and Examples set out below.

*Caulobacter* strains that are incapable of forming an S-layer, including those which shed the S-layer protein upon secretion, may be used in this invention. Examples are the S-layer negative mutants CB2A and CB15AKSac described in Smit, J., and N. Agabian (1984) J. Bacteriol. 160:1137–1145; and, Edwards, P., and J. Smit (1991) J. Bacteriol. 173:5568–5572. Examples of shedding strains are CB15Ca5 and CB15Ca10 described in Edwards and Smit (1991), and be smooth lipopolysaccharide deficient mutants described in Walker. S. G. et al. (1994) J. Bacteriol. 176:6312–6323.

A heterologous polypeptide as referred to herein may be any peptide, polypeptide, protein or a part of a protein which is desired to be expressed in *Caulobacter* and which may be secreted by the bacterium. A polypeptide that is heterologous to a surface layer protein of a *Caulobacter* means a polypeptide not found in the surface layer protein native to the *Caulobacter* in which the heterologous polypeptide is expressed.

Heterologous polypeptides include enzymes and other functional sequences of amino acids as well as ligands, antigens, antigenic epitopes and haptens. The size of the heterologous polypeptide will be selected depending upon whether an intact S-layer is to be produced in the *Caulobacter* or whether the protein to be recovered from the bacterial medium as described below. Heterologous polypeptides of about 400 amino acids have been expressed. Preferably, the cysteine content of the heterologous polypeptide and the capacity for formation of disulphide bonds within is the chimeric protein will be kept to a minimum to minimize disruption of the secretion of the chimeric protein. However, the presence of cysteine residues capable of forming a disulphide bond which are relatively close together, may not affect secretion.

This invention may be practiced by implementing known methods for insertion of a selected heterologous coding sequence into all or part of an S-layer protein gene so that both the S-layer protein and the heterologous sequence are operably linked thereby permitting the S-layer protein and the heterologous sequence to be transcribed together and "in-frame". Sequencing of an S-layer protein gene permits one to identify potential sites to install heterologous genetic material. The repetitive nature of the protein in the S-layer permits multiple copies of heterologous polypeptides to be expressed.

The following general procedure lays out courses of action, with reference to particular plasmid vectors or constructions, that may be used to accomplish fusion of an S-Layer protein with a polypeptide of interest. The following description makes reference to the rsaA gene of *C. crescentus* described by Gilchrist, A. et al. (1992) and in WO 97/34000, as an example.

The general procedure includes detailed steps allowing for the following possibilities:
 (1) use of a collection of potentially permissive sites in the S-layer gene to install the genetic information for a polypeptide of interest;
 (2) use of a carrier cassette for delivering a gene of interest to sites within the S-layer gene;
 (3) creation of a collection of random insertion sites based on a restriction enzyme of choice, if the available collection of potentially permissive sites is for some reason unsuitable; and,
 (4) direct insertion of DNA coding for a polypeptide of interest into permissive sites.

The general procedure involves the following steps and alternative courses of action. As a first step the practitioner may choose an appropriate region (or specific amino acid position) of the S-layer for insertion of a desired polypeptide. Second the practitioner will create a unique restriction site (preferably hexameric) in the S-layer gene at a position within the gene encoding that region (or corresponding to a specific amino acid) using either standard linker mutagenesis (regional) or site directed mutagenesis (specific amino acid). The unique restriction site will act as a site for accepting DNA encoding the polypeptide of interest. For example, the plasmid-based promoter-less version of the rsaA gene (pTZ18U:rsaA P) described in Gilchrist. A. et al. (1992) may be used because it contains an appropriate combination of 5' and 3' restriction sites useful for subsequent steps. Preferably, the restriction site should not occur in the S-layer gene, its carrier plasmid or the DNA sequence coding for the polypeptide of interest.

If it is unclear which region of the S-layer would be suitable for insertion of a polypeptide of interest, a random linker mutagenesis approach may be used to randomly insert a unique linker-encoded restriction site (preferably hexameric) at various positions in the gene. Sites for insertion of the linker are created using an endonuclease, either of a sequence specific nature (e.g. tetrameric recognition site restriction enzyme) or sequence non-specific nature (e.g. Deoxyribonuclease I [DNase I]). A particularly suitable method is the generalized selectable linker mutagenesis approach described in Bingle, W. H., and J. Smit. (1991) Biotechniques 10: 150–152, by which endonuclease digestion is carried out under partial digestion conditions and a library of linker insertions at different positions in a gene is created. Partial digestion with different endonucleases create potential sites for insertion of a linker.

If restriction endonucleases are used to create sites for subsequent insertion of a linker encoding a hexameric restriction site, mutagenesis may also be done with a mixture of 3 different linkers incorporating appropriate spacer nucleotides in order to obtain an insertion with proper reading frame at a particular restriction site. With DNase I, only one linker is needed, but only 1 of 3 linker insertions may be useful for accepting DNA encoding the polypeptide of interest depending on the position of to DNase I cleavage.

A linker tagged with a marker may be used to insert DNA of interest at a restriction site. For example, if BamHI sites are appropriate is sites for the introduction of DNA encoding a polypeptide of interest. BamHI linkers tagged with a kanamycin-resistance gene for selectable linker mutagenesis may be used. One such 12-bp linker carried in plasmid pUC1021K for use in rsaA was described by Bingle and Smit (1991). Two additional 15-bp linkers (pUC7165K and pTZ6571K) for creating 2 other possible translation frames within the linker insert itself are described in FIGS. 3 and 4 of WO 97/34000. A mixture of three such linkers is preferably used for mutagenesis.

Once a library composed of linker insertions encoding desired a hexameric restriction site at different positions has been created, DNA encoding a polypeptide of interest may be inserted into the sites en masse. The library may be digested with the restriction enzyme specific for the newly-introduced linker encoded restriction site and ligated to a DNA fragment encoding the polypeptide of interest and carrying the appropriate complementary cohesive termini. DNA specifying the polypeptide of interest can be prepared by a cumber of standard methods, which may include oligonucleotide synthesis of 2 anti-complementary strands, polymerase chain reaction (PCR) procedures, or addition of linkers whose termini are compatible with the introduced sites in the target gene to a suitably modified segment of DNA.

In order to facilitate the rapid recovery of genes carrying DNA inserted at restriction sites, a carrier oligonucleotide may be used. An example of the use of such a carrier, shown in FIG. 1 of WO 97/34000, was designed to accept DNA prepared by PCR or by anneating synthesized oligonucleotides and controls direction of insertion of the foreign segment into a rsaA gene through use of a promoterless drug resistance marker. The DNA of interest is first directionally cloned, if possible, using the XhoI, StuI, or SalI sites or non-directionally cloned using any one of the sites in the same orientation as a promoterless chloramphenicol resistance (CmR) gene. To do this the DNA of interest may be provided with the appropriate termini for cloning and spacer nucleotides for maintaining correct reading frame within the cassette and should not contain a BglII site. For insertion into the BamHI linker library, the DNA of interest is recovered as a BamHI fragment tagged with a CmR gene. When ligated to the BamHI digested rsaA linker library, only those colonies of the bacterium (eg. E. coli) used for the gene modification steps that are recovered will be those carrying insertions of the desired DNA in the correct orientation, since the promoter on the plasmid is 5' to rsaA P and the CmR gene. This eliminates screening for DNA introduction and increases the recovery of useful clones. While still manipulating the library as one unit, the CmR gene is removed using BglII. The carrier oligonucleotide also provides the opportunity to add DNA 5' or 3' to the DNA of interest at SalI, XhoI or StuI sites providing the DNA of interest does not contain any of these sites. This allows some control over spacing between rsaA sequences and the sequence of the DNA of interest.

Genes carrying the DNA of interest in the correct orientation may be excised from the plasmid and transferred to a suitable vector providing a promoter recognized by *Caulobacter*. Such vectors include pWB9 or pWB10 with EcoRI/SstI sites, as described in Bingle, W. H., and J. Smit. (1990). Plasmid 24: 143–148. The DNA of interest should not contain the same restriction sites present in the vector. This allows expression of the hybrids in S-layer negative mutants of *Caulobacter*.

*Caulobacter* surviving transfer are examined for chimeric protein secretion, and optionally S-layer assembly or presentation of the new polypeptide activity, antigenicity, etc. on the cell, by methods specific to the needs of the investigator or the capabilities of the inserted sequence. Many of the sites created are "benign" as they have no effect on the functional regions of the protein involved with export, self assembly, etc. However, not every site that results in an absence of functional disruption of the S-layer is best for insertion of new activities. Some sites may not be well exposed on the surface of the organism and other sites may not tolerate insertion of much more DNA than the linker sequence.

It is possible to express single or multiple insertions of heterologous polypeptides in a S-layer chimeric protein which will still assemble as an S-layer on the cell surface. Some sites may be sensitive to even small insertions resulting in the chimeric protein being released into the medium. Release may also be deliberately effected by use of a shedding strain of *Caulobacter* to express the chimeric protein or by physical removal of the S-layer from whole cells. Where S-layer assembly is not required, quite large polypeptides may be expressed as part of the S-layer protein. Expressing a chimeric protein containing a S-layer protein component having substantial deletions, may increase the size of the heterologous polypeptides that will be expressed and secreted by *Caulobacter*.

The preceding methods describe insertion of linkers in-frame into a promoterless version of the S-layer gene. The sites that are introduced allow subsequent insertion of foreign DNA in-frame into the full length gene. This invention also involves the construction of chimeric S-layer protein genes and the resulting production of chimeric S-layer proteins in which The S-layer gene component lacks large portions of the gene. This reduces the amount of *Caulobacter* protein present in the secreted chimeric protein. Generally, large deletions throughout the S-layer gene will result in a chimeric protein that is not capable of forming an S-layer. Attachment of the S-layer to the cell is abolished if the N-terminal amino acids which contribute to S-layer formation are deleted. For example deletion of the first 29 N-terminal amino acids of the RsaA protein will accomplish this. Also absence of the first 776 amino acids from the N-terminal region of RsaA will result in a chimeric protein secreted from the cell but having a S-layer component consisting of only the 250 C-terminal amino acids of RsaA. Since only the extreme C-terminal region corresponding to approximately amino acids 945–1026 of RsaA is required for secretion of an S-layer chimeric protein from *C. crescentus* use of only the C terminal secretion signal will prevent S-layer formation. Furthermore use of only am 15 the C-terminal region promotes spontaneous aggregation of much of the secreted chimeric protein in the cell medium and formation of a macroscopic precipitate that may be collected with a course mesh or sheared to micron-sized particles. Yields of up to 250 mg. (dry weight) of protein per liter of cells may be possible.

Sequence analysis of the 3' region of the S-layer genes from different strains of *C. crescentus* shows that the portion of the gene encoding the C-terminal region of the S-layer protein is highly conserved within the species. It has now been determined that while there is moderate variability in the sequence of surface layer proteins (including the secretion signal) from different species of freshwater *Caulobacter*, there is an unusually high sequence conservation among different *Caulobacter* species for the ABC-transporter protein and the membrane fusion protein. Sequence analysis of CB15 and CB2A (readily distinguishable strains of *C. crescentus*) shows identical DNA sequences coding for the last 118 amino acids of the RsaA protein (which includes the secretion signal) and sequencing of the next downstream translated gene (rsaD) to amino acid 97 of the gene product shows only a single base pair change, resulting in a conservative amino acid substitution in the ABC transporter protein. Sequence analysis of surface layer protein genes and the transporter protein genes in species other than *C. crescentus* shows more variability in the secretion signals between species as compared to strains of *C. crescentus*. However, a much higher level of inter-species conservation exists with respect to the transporter proteins, even (as is the case with some species of *Caulobacter*) when the transporters are not located immediately downstream from the surface layer protein gene.

It having now been demonstrated that species of *Caulobacter* other than *C. crescentus* employ a C-terminal secretion signal for the surface layer protein and contain highly conserved transport proteins, the procedures described herein or are known in the art may be readily employed for use surface layer protein secretion signals from *Caulobacter* other than *C. crescentus* and to identify and use species other than *C. crescentus* as a host for expression of heterologous polypeptides.

The moderate inter-species conservation of surface layer protein genes (particularly for glycine-aspartic acid rich regions of the protein) may be exploited for locating a S-layer protein gene in a candidate *Caulobacter*, using known methods. Alternatively, the gene may be located by searching for a sequence hybridizable to a sequence derived from an amino acid sequence which is determined by sequencing the S-layer protein secreted by the candidate cell, using methods in the known art.

The minimal amino acid tract from a *Caulobacter* that constitutes the essential surface layer protein secretion signal may be determined by the procedures described herein or by methods known in the art. One approach is to identify regions from S-layer genes of a *Caulobacter* which code for amino acid sequences that exhibit some identity to the last 82 C-terminal residues of the RsaA protein of *C. crescentus*. Homology to upstream sequences in the protein may also be assessed. Another approach is to delete N-terminal amino acids from the surface layer protein until secretion is lost.

*Caulobacter* other than *C. crescentus* may be screened for suitability as hosts for expression and secretion of heterologous polypeptides by determine whether a candidate cell has a gene or gene product which exhibits sufficient identity to the rsaD or rsaE genes or RsaD or RsaE proteins from *C. crescentus*. This may be conveniently accomplished by determining whether a oligonucleotide probe based on the rsaD or rsaE gene sequences will selectively hybridize to DNA from the candidate cell. The probe is prepared by any means for construction of an oligonucleotide and will preferably have a sequence that is homologous to all or pan of rsaD or rsaE. The probe will consist of at least 20, more preferably at least 30, more preferably at least 40, and even more preferably at least 50 nucleotides. The probe may be used for amplification by known procedures (eg. by PCR) of target DNA or may be labelled for direct determination of the presence of target DNA by known procedures. Labels include radio-labels, fluorescent labels, etc. Detection of target DNA may be accomplished through various standard techniques such as Southern blotting, in-situ hybridization, etc. *Caulobacter* other than *C. crescentus* are useful as host organisms for expression and secretion of heterologous polypeptides when the host contains a transport protein that is homologous to either the RsaD or RsaE proteins of *C. crescentus*.

An amino acid or nucleic acid sequence is "homologous" to another such sequence if the two sequences are substantially identical and the function of the sequences is conserved (for example, both sequences function as or encode a secretion signal or transport protein functional in *Caulobacter*). Two amino acid or nucleic acid sequences are considered substantially identical if they share at least about 70% sequence identity, preferably at least about 80% sequence identity, more preferably at least about 90% sequence identity. Sequence identity may be determined using the BLAST algorithm, described in Altschul et al. (1990), J. Mol. Biol. 215:403–10 (using the published default settings). In such circumstances, percentage of sequence identity may be expressed as a "homology" of the same percentage.

An alternative indication that two nucleic acid sequences are homologous (substantially identical) is when two sequences selectively hybridize to each other under at least moderately stringent conditions. Hybridization to fitter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel et al. (eds), 1989, *Current Protocols in Molecular Biology*, Vol. 1, Green Publishing Associates, Inc., and John Wiley & Sons, Inc., New York, at page 2,10.3). Higher sequence identity is demonstrated by hybridization to filter-bound sequences under stringent conditions which may (for example) be performed in 0.5 M $NaHPO_4$, 7% SDS, 1 mM EDTA at 65° C., and washing in 0.1×SSC/0.1% SDS at 68° C. (see Ausubel, et al. (eds), 1989). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part 1, Chapter 2 "Overview of Principles of Hybridization and the Strategy of Nucleic Acid Probe Assays", Elsevier, New York). Generally, stringent conditions are selected to be about 5° C. lower than the thermal melting point for the specific sequence at a defined ionic strength and pH.

In this invention, screening of *Caulobacter* for use as a host organism according to transport protein sequence identity may involve the use of oligonucleotide probes designed to selectively hybridize to target DNA, if the target contains DNA that is homologous (substantially identical) to all or part of rsaD or rsaE. *Caulobacter* of this invention comprise DNA encoding a transport protein that is homologous to either rsaD or rsaE. However, as disclosed herein surface layer protein secretion signals useful in this invention may not exhibit such high identity to the secretion signal of the rsaA gene. The level of identity to RsaA or rsaA sequences might be less than 50%, which is lower than that required for "homology" as defined above. In such cases, the secretion signal may be solely defined according to is ability to effect transport of a protein of which the signal is the C-terminus, through the type I secretory system of a *Caulobacter*. The presence or absence of this function may be readily determined by monitoring extra-cellular occurrence of a protein of interest using known means or the procedures described herein.

Expression of heterologous polypeptides may be practiced by use of modified S-layer genes borne on plasmids which may be readily constructed and introduced to *Caulobacter* by electroportation. Typically, the plasmid is maintained in the *Caulobacter* by antibiotic selection. Highly modified, S-layer genes with attached heterologous sequences may also be introduced into *Caulobacter* on a plasmid that is not replicated by *Caulobacter* since homologous recombination of the incoming modified S-layer gene with the chromosome-resident copy of the S-layer gene in the cell will often occur at a low but practicable frequency resulting in a gene rescue or transfer event. In some cases it may be desirable to obtain a stable cell line in which the chimeric S-layer gene is chromosomal. Various protocols for creating chromosomal insertions are set out in the Examples.

Use of *Caulobacter* S-layer protein as a vehicle for production of a heterologous polypeptide has several advantages. Firstly, the S-layer protein is synthesized in large quantities and has a generally repetitive sequence. This permits the development of systems for synthesis of a relatively large amount of heterologous material as a fusion product with an S-layer protein (chimeric protein). It may be desirable to retain the chimeric protein as part of the bacterial cell envelope or, the fusion product may be separated from the organism, such as by the method described in: Walker, S. G. et al. (1992) J. Bacteriol. 174:1783–1792. Alternatively, the *Caulobacter* strain that is used to express the fusion product may be derived from a strain such as CB15Ca5 that sheds its S-layer.

*Caulobacter* are particularly suited for use in bioreactor systems. An example would be the use of a modified *Caulobacter* to treat sewage, waste water etc. *Caulobacters* are ideal candidates for fixed-cell bioreactors, the construction of which is well-known (eg. rotating biological contactors). Other bacteria often produce copious polysaccharide slimes that quickly plug filtration systems. In some cases, other bacteria are not surface-adherent. By taking advantage of the natural bio-film forming characteristics of *Caulobacter*, bioreactors may be formed comprising a substrate and a single layer of cells adhered thereon with the cells distributed at high density. A variety of substrates may be used such as a column of chemically derivatized glass beads or a porous ceramic material such as ceramic foam.

Another application is in the production of batch cultures of modified *Caulobacter* wherein the S-layer protein is a fusion product with an enzyme. For example, such *Caulobacter* could be grown in wood pulp suspensions at an appropriate juncture of the pulping process in order to provide for enzymatic decomposition of the wood-pulp structure.

Examples of enzymes that may be expressed as chimeric S-layer proteins include alkaline phosphatase (eg. by expression of the pho A gene of *E. coli*; see: Hoffman, C. S., and Wright, A. (1985) Proc. Natl. Acad. Sci. U.S.A. 82:5107–5111; Bingle, W. H., et al. (1993) Can. J. Microbiol.39:7080; and, Bingle, W. H. and Smit, J. (1994) Can. J. Microbiol. 40:777–782.) and, cellulase (eg. by expression of the CenA gene of *Cellulomonas firni*; see: Bingle, W. H. et al. (1993): and, Bingle, W. H. and Smit, J. (1994).

Another application is the production of organisms that secrete and optionally present vaccine-candidate epitopes. Modified *Caulobacter* may be readily cultured in outdoor freshwater environments and would be particularly useful as fish vaccines. The two-dimensional crystalline array of the S-protein layer of *Caulobacter*, which has a geometrically regular, repetitive structure, provides an ideal means for dense packing and presentation of an epitope as part of an intact S-layer on the bacterial cell surface.

Polypeptides secreted by *Caulobacter* may be harvested in large quantities, relatively free of contaminants and protein of host cell origin. Expression of a heterologous polypeptide fused with sufficient C-terminal amino acids of the S-layer protein to promote secretion of the protein results in the accumulation of large quantities of secreted product in the cell medium. The chimeric protein does not have to be released from the cell surface, but adjustment of the size of the S-layer protein portion can dictate whether the secreted chimeric protein is soluble or will precipitate in the cell medium. This is useful in cases where the *Caulobacter* is used to express a foreign antigenic component and it is desired to minimize the amount of host cell protein associated with the antigen.

EXAMPLE 1

Production of Permissive Insertion Sites in *C. crescentus*

Using the restriction enzyme TaqI, a partial digestion of the rsaA gene in pTZ18U:rsaA P produced a group of linearized segments with random TaqI sites cleaved. The linearized segments were modified by use of the tagged linker mutagenesis procedure of Bingle and Smit (1991), using the 12-bp BamHI linker carried in plasmid pUC102K discussed in the general procedure above. Those products that produced a full-length protein in *E. coli* were ultimately transferred to pWBI (a minor variation of pWB9 that is replicated by *Caulobacter*), as described in the general procedure. The resulting construction was introduced into a *C. crescentus* strain. Distinguishable events were retrieved and analyzed for the ability to produce a full-length protein in *C. crescentus* and to produce the crystalline S-layer on their surface and the approximate location of the insertion. Cells were screened for the presence of a S-layer protein of approximately 100 kDa that is extracted from the surface of whole cells by 100 mM HEPES at ph2. The results of this screening resulted in five successful events.

The five positive events represented cases where a 4-amino acid insertion was tolerated with no effect on the S-layer function. The S-layers of the modified *Caulobacter* were indistinguishable from a wild-type S-layer. By producing 3 versions of the gene of interest, representing each possible reading frame (using standard linker addition technology), one may test each of these sites for suitability in expressing the desired activity. Also, by using restriction enzymes other than TaqI (such as AciI, HinPI or MspI) a larger library of BamHI insertions may be created.

EXAMPLE 2

Investigation of Other Permissive Sites in rsaA Gene

A library of 240 BamHI linker insertions was created using the procedures of Example 1. Of the 240 insertions, 45 target sites in the rsaA gene were made with TaqI. 34 of the latter insertions were discarded because the clones contained deletions of rsaA DNA as well as the linker insertions. The remaining 11 resulted in 5 non-permissive and the 5 permissive sites found in Example 1. The remaining 195 insertions in the library were made using the enzymes HinPI, AciI, and MspI to create target sites as outlined in Example 1. Of the latter 195 insertions. 49 permissive sites were located for a total of 55. Of those sites scored as non-permissive, some may have had deletions of rsaA DNA at the linker insertion site. One BamHI linker insertion at a TaqI site thought to be permissive was later found by nucleotide sequencing to be located outside the rsaA structural gene reducing the total number of permissive sites to 54 from 55. The results show that sites that will accept 24 amino acids while still allowing the protein to be made and assembled into an S-layer are scattered up and down the protein. There is a high proportion of sites at which such insertions do not prevent expression and assembly of the S-layer. Approximately 25–50% of in-frame linker insertions will be tolerated by the S-layer protein and the *Caulobacter* and that diverse regions of the protein will tolerate insertions.

EXAMPLE 3

Studies with Cadmium Binding Polypeptides

Following the foregoing procedures, single and multiple copies of DNA encoding a synthetic cadmium binding peptide were synthesized, inserted at the amino acid 277 site of rsaA using the above described Carrier cassette, and expressed in *C. crescentus*. The peptide has a single cysteine residue. Mild acid extracts of whole cells expressing the modified gene were subjected to SDS-PAGE for identification of S-layer proteins. The S-layer protein was expressed and secreted when there was from 1 to 3 copies of the cadmium binding peptide present at RsaA amino acid position 277. Insertion of 4 or more copies resulted in a dramatic reduction of S-layer protein released from the whole cells by mild acid treatment to barely detectable levels. Detection by autoradiography of RsaA protein in vivo labelled with $^{35}$S-cysteine and in vitro with $^{125}$I- iodoacetamide confirmed that the cadmium binding peptide was part of the chimeric protein. This demonstrates that C. crescentus is capable of secretion of a chimeric rsaA protein having a limited cysteine content and a limited capacity for disulphide bond formation but that increased capacity of disulphide bond formation will limit production.

EXAMPLE 4

Expression and Presentation of Antieenic Epitopes on Caulobacter Cell Surface

Using the library of the 49 permissive sites other than those made with TaqI described in Example 2, the coding sequence for a 12-amino acid pilus peptide epitope lacking cysteine residues from Pseudomonas aeruginosa PAK pilus (described in FIG. 8 of WO 97/34000) was inserted at the sites using the procedures described above, employing the carrier cassette described above. Positioning of the inserted DNA between the first Bam HI site and the Bgl II site permitted use of the latter site for making repeated insertions of DNA. DNA coding for the PAK pilus peptide was prepared by oligonucleotide synthesis of two anti-complementary strands.

The transformed bacteria were screened for both production and presentation of the epitopes by the transformed Caulobacter using standard Western immunoblot analysis (see: Burnette, W. N. (1981) Analytical Biochemistry 112:195–203) and by colony immunoblot tests in which the cells were not disrupted (see: Engleberg, N. C., et al. (1984) Infection and Immunity 44:222–227). Anti-pilus monoclonal antibody (PK99H) obtained from Dr. Irvin, Dept. of Microbiology, University of Alberta, Canada was used in the immunoblot analyses to detect the presence of the pilus epitope insert. The antibody was prepared using purified Pseudomonas aeruginosa PAK pilus as the antigen and a monoclonal antibody was isolated by standard techniques using BALB/C mice as a source of ascites fluid. Reaction with the antibody in a whole cell colony immunoblot assay showed that the epitope is not only expressed in the transformed Caulobacter but is exposed on the S-layer surface overlying the cell in such a way that the epitope is available to the antibody. When two cysteine residues of the pilin epitope were incorporated in the chimeric protein, the protein was still expressed and secreted at normal levels.

Of the organisms screened, insertions of the pilus epitope at the following sites in the rsaA gene as determined by nucleotide sequencing resulted in a positive reaction with the antibody in the whole cell Colony immunoblot analysis: 69, 277, 353, 450, 485, 467, 551, 574, 622, 690, 723, and 944. The results show that the permissive sites that will accept polypeptides of the size of the epitope are numerous and scattered across the gene.

Further studies with the pilus peptide resulted in successful expression and secretion of chimeric proteins having single copies of the peptide at various other locations. Also, four and seven copies of the peptide were expressed and secreted as a RsaA chimeric protein when inserted at amino acids 277 and 551 respectively of the RsaA protein. However, insertions of the peptide at amino acids 69, 277, 450, 551 and 622 resulted in a chimeric protein that did not attach to the cell surface and was released into the culture medium.

EXAMPLE 5

Insertion of Large Polypeptides

Bacterial surface proteins from organisms other than Caulobacter are generally not known to accept polypeptides larger than about 60 amino acids within the structure of the surface protein. The procedures of the preceding Example were carried out in order to insert the coding sequence of a 109 amino acid epitope from IHNV virus coat glycoprotein at the same insertion sites. The IHNV epitope was prepared by PCR and had a sequence as shown in FIG. 9 of WO 97/34000, which is equivalent to amino acid residues 336444 of the IHNV sequence described in: Koener, J. F. et al. (1987) Journal of Virology 61:1342–1349. Anti-IHNV polyclonal antibody against whole IHNV obtained from Dr. Joann Leong, Dept. of Microbiology, Oregon State University, U.S.A. (see: Xu, L. et al. (1991) Journal of Virology 65:1611–1615), was used in immunoblot assays as described above to screen for *Caulobacter* that express and present the IHNV sequence on the cell surface. Reaction in the whole cell colony immunoblot assay was positive in respect of insertions at sites 450 and 551, and negative at a site which was at approximately amino acid 585.

The IHNV insert contains a single cysteine residue and is an extremely large insert for successful expression as a fusion product with a bacterial surface protein. In further studies, the same 109 amino acid portion of the IHNV glycoprotein was inserted at amino acid 450 of the RsaA protein. The protein secreted by *C. crescentus* was recovered from the cell culture medium. SDS-PAGE analysis showed that some of the protein was smaller than the predicted rsaA chimeric protein but still bound the anti-IHNV antibody. Analysis of these proteolytic products showed that cleavage of the chimeric protein occurred at an Arg residue encoded by the gene transfer cassette. Thus in some cases, adjustment of the nucleotide sequence at the interface of the polypeptide and rsaA coding sequences may be necessary to prevent expression of an arginine residue.

EXAMPLE 6

Methods are described above for the insertion of 12-bp BamHI linker sites into a promoterless version of the rsaA gene. Because linker insertions involve the insertion of 12 bp (a multiple of three), an in-frame linker insertion resulted in every case. These linker sites are introduced to allow subsequent insertion of DNA encoding foreign peptide/proteins. Expression of such chimeric genes leads to the production of an entire full-length RsaA protein carrying the inserted heterologous amino acid sequence of interest. A number of BamHI site positions were identified above precisely by nucleotide sequencing. Four of the sites in the rsaA gene correspond to amino acid positions 188, 782, 905, 944 in the RsaA protein. For this example, an additional linker insertion was created at amino acid position 95 of the native gene (i.e. this gene carried its own promoter) using the same methodology. All five in-frame BamHI linker insertion sites were inserted in the rsaA so that the nucleotides of the linker DNA were read in the reading frame GGA/TCC.

Because all BamHI linker nucleotides were read in the same reading frame the 5' region of one rsaA gene carrying a BamHI linker insertion at one position could be combined with the 3' region of an rsaA gene carrying another of the BamHI linker insertions to create in-frame deletions with a BamHI site at the joint between adjacent regions of rsaA. Using such a method, in-frame deletions of rsaA (AA95–782) and rsaA(AA188–782) were created.

DNA fragments encoding various C-terminal portions of the 1026 amino acid RsaA protein were isolated using the newly inserted BamHI linker sites as the 5' terminus of the fragment and a HindIII site as the 3' terminus of the fragment. These BamHI fragments were transferred to the BamHI/HindIII sites of pUC8 (J. Vieira, and J. Messing. (1982) Gene 19:259–268) creating rsaA C-terminal segment carrier plasmids (see FIG. 12 of WO 97/34000). The insertion into pUC8 also resulted in the creation of an in-frame fusion between the first 10 N-terminal amino acids of LacZa and the various C-terminal fragments (AA782–1026, AA905–1026 or AA944–1026) of RsaA. These LacZa:rsaA fusion proteins can be produced in *Caulobacter* using the lacZa transcription/translation initiation signals when introduced on appropriate plasmid vectors or direct insertion into the chromosome (see: W. H. Bingle, et al. (1993) Can. J. Microbiol. 39:7080).

Both types of construction, the deletion versions and the C-terminal only segments, resulted in the production of proteins secreted by the *Caulobacter* as highly modified S-layer proteins. The gene segments can also facilitate the secretion of heterologous polypeptides by insertion or fusion of appropriate DNA sequences at the unique BamHI site that exists in each of the constructions, as described below.

A Creating Fusions of Desired Sequences with C-terminal Portions of a *Caulobacter* S-layer Gene-Method 1

The process may be as follows:

(1) Inserting the desired sequence into the Carrier cassette. Heterologous sequences may be introduced into a carrier by:

(a) Insertion of a single copy of the desired gene segment.

Depending upon the length of a gene segment, two methods of construction may be used. For segments of up to about 30 amino acids, two oligonucleotides of appropriate sequence may be chemically synthesized, annealed by mixing, heating and slow cooling and ligated into the carrier cassette. The oligonucleotides will also contain additional base pairs that recreate "sticky ends" of appropriate restriction endonuclease sites at each end of the duplex DNA that results from the annealing process.

For longer segments, PCR may be used to amplify a region of a target DNA sequence. Oligonucleotides are synthesized that have sequence complementary to the boundaries of the desired sequence and which contain additional base pairs that recreate a "sticky end" of an appropriate restriction endonuclease site. In the present example oligonucleotides are made to produce products with the appropriate restriction endonuclease site for directional cloning into the carrier cassette. PCR amplification of the desired sequence is then done by standard methods.

For each method, sticky ends must be appropriate for restriction sites at the 5' terminus and the 3' terminus. This places the desired gene segment in the correct orientation within the carrier cassette. Reading frame continuity is maintained by appropriate design of the oligonucleotides used for the PCR step.

(b) Preparation of multiple copies of the desired gene segment.

The carrier cassette also allows for production of multiple insert copies. For examples a restriction site in the cassette may be restored after removal of a promoterless antibiotic resistance gene and the site is then used to insert an additional copy as described in WO 97/34000. This "piggyback" insertion still maintains the correct reading frame throughout the construction. Any number of additional cycles of "piggy-backing" can be done because the ligation results in a sequence which is no longer a substrate for the restriction enzymes. The result is the production of cassettes of multiple copies of the desired sequence which can be transferred to appropriately modified S-layer protein genes with the same ease as a single copy. An additional feature of this method is that different heterologous sequences can be paired together in this multiple copy cassette with the same ease as multiple copies of the same heterologous sequence.

EXAMPLE 6a

Insertion of an 109 Amino Acid Segment of the IHNV Surface Glycoprotein to Carrier Cassette.

A PCR product was made that contained the DNA coding for amino acids 336 to 444 of the major surface glycoprotein of the Infectious Hematopoietic Necrosis Virus (IHNV), as described in WO 97/34000.

EXAMPLE 6b

Insertion of an 184 Amino Acid Segment of the IHNV Surface Glycoprotein to Carrier Cassette A PCR product was made that contained the DNA coding for amino acids 270 to 453 of the IHNV glycoprotein segment.

EXAMPLE 6c

Insertion of Single and Multiple Copies and an Epitope of the *Pseudomonas aeruginosa* PAK Pilus Gene to Carrier Cassette Oligonucleotides were constructed to code for the pilus epitope described in Example 4. Using the methods outlined in part A(1)(b) of this Example. 3 tandem copies were prepared.

(2) Transfer of Carrier Cassette to C-terminal Segment Carrier Plasmids. The constructs described in Examples 6a and 6b were transferred to a rsaA C-terminal Segment carrier plasmid, as described above, resulting in an in-frame fusion of: (a) a amino acid section of the β-galactosidase protein, (b) the desired sequence flanked by 2–3 amino acids derived from the carrier cassette sequence, and (c) the appropriate rsaA C-terminal segment. In some cases, the first codon of the rsaA C-terminal segment is converted to a different codon as a result of the fusion. For example, while the rsaA C-terminal segment may have coded for amino acids 944–1026 of RsaA, the resulting chimeric protein may only have amino acids 945–1026 native to RsaA.

EXAMPLE 6d

Fusion of Carrier/109 AA and 184 IHNV Segments to C-terminal rsaA Segment AA782–1026.

This was done using the carrier cassettes described in Examples 6a and 6b and the AA782–1026 rsaA C-terminal segment carrier plasmid described above.

EXAMPLE 6e

Fusion of Carrier/109 AA and 184 AA IHNV Segments to C-terminal rsaA Segment AA905–1026.

This was done using the carrier cassettes described in Examples 6 a and 6b and the AA905–1026 rsaA C-terminal segment carrier plasmid described above.

EXAMPLE 6f

Fusion of Carrier/109 AA and 184 AA IHNV Segments to C-terminal rsaA Segment AA944–1026.

This was done using the carrier cassettes described in Examples 6a and 6b and the AA944–1026 rsaA C-terminal segment carrier plasmid described above.

EXAMPLE 6g

Fusion of Carrier/3× Pilus Epitope Segment to C-terminal rsaA Segment AA782–1026.

This was done using the carrier cassettes described in Example 6c and the AA782–1026 rsaA C-terminal segment carrier plasmid described above.

(3) Expression of the Desired Fusion in an Appropriate Caulobacter Host Strain.

(a) Plasmid-based expression.

To create plasmid vectors that can be introduced and maintained in *Caulobacter*, an entire C-terminal segment carrier plasmid may be fused to a broad host range vector such as pKT215 or pKT210 (see: M. Bagdasarian, et al. (1981) Gene 16:237–247) using the unique HindIII restriction site present in each plasmid. The resulting plasmid is introduced into *Caulobacter* by conjugation or electroporation methods and is maintained by appropriate antibiotic selection.

The fusions described in Examples 6d–6 g were expressed in *C. crescentus*. In each case expression and secretion of the chimeric S-layer protein was detected by Western immunoblot analysis of electrophoretic gels of the cell culture supermutant employing the monoclonal antibody for each of the polypeptide epitopes. The transporter signal is localized to amino acids 945–1026 of the S-layer protein since all the chimeric proteins in the Examples were secreted. Precipitation of the chimeric protein occurred with the use of rsaA segment AA782–1026 but not AA944–1026. Recovery of precipitate using AA905–1026 was reduced as compared to AA782–1026.

(b) Selection of appropriate *C. crescentus* host strains.

It is often desirable to use a S-layer negative host strain such as CB2A or CB15aKSac. If it is important to ensure that the fusion protein is not attached to the cell surface, the use *C. crescentus* strains CB15Ca5KSac or CB15Ca10KSac may be appropriate. The latter strains have additional mutations that result in the loss of the production of a specific species of surface lipopolysaccharide that has been demonstrated to be involved with the surface attachment of native S-layer protein as a 2-dimensional crystalline array (see: Walker S. G. et al. (1994) J. Bacteriol. 176:6312–6323). With highly modified versions of an S-layer gene, this provision is not necessary since virtually all regions of the gene that may have a role in the attachment process will be absent.

An example of a growth media well suited to both propagation of *Caulobacter* for general purposes (including cloning steps) and also to produce the secreted and aggregated chimeric proteins is PYE medium, a peptone and yeast extract based medium described in Walker et al., (1994).

B. Creating Fusions of Desired Sequences with C-terminal Portions—Method 2

Methods other than the use of a carrier cassette plasmid are possible for creation of heterologous insertions into deletion, versions of a S-layer gene or fusions with C-terminal portions of a S-layer protein. PCR may be used or other known methods may be used. The general procedure is as follows:

(1) Use of PCR to prepare appropriate segments:
  (a) Preparation of amplified segment with appropriate ends may be carried out in a manner similar to that described part A(1)(a) of this example. Oligonucleotides are designed and synthesized such that they will anneal to appropriate regions of the desired heterologous DNA and also contain "sticky ends" of appropriate sequence and frame so that the resulting PCR product can be directly inserted into appropriate modified S-layer genes.
  (b) Transfer to appropriate C-terminal segments may be carried out by inserting the PCR products into selected C-terminal segments such as AA782–1026, AA905–1026, or AA944–1026, as described in Examples 6d–6g. In addition to the BamHI site described, the EcoR1 restriction site could also be used as the 5' terminus of the incoming PCR segment, since this site is also available in the pUC8 vector and not in the S-layer gene, so long as the correct reading frame was maintained when designing the oligonucleotides used to prepare the PCR product.

(2) Expression of the desired fusion in an appropriate *Caulobacter* host strain may be carried out using the procedures outlined in part A(3) of this example.

C. Creating Insertions of Desired Sequences into Versions of a S-layer Gene Having Large Internal In-frame Deletions.

The general process may be as follows, with reference to rsaA:

(1) Creating Appropriate In-frame Deletions rsaA (AA95–782) and rsaA(AA188–782) may be prepared as described above. Because most of the BamHI linker insertion sites are in the same reading frame with respect to each other, it is possible to combine other pairs of 5' and 3' segments using the same general method, with the same result of maintenance of correct reading frame throughout. These deletion versions may then be tested individually to ensure that S-layer protein is still secreted by the *Caulobacter*.

(2) Insertion of a Gene Segment carrier Cassette Containing the Desired Sequences: insertion and transfer of carrier cassettes may be done using the procedures described in parts A(1) and A(2) of this example.

EXAMPLE 6h

Insertion of the 109 AA IHNV segment into rsaA (AA95–782) and insertion of the 109 AA IHNV segment into rsaA(AA188–782) may be carried out as in Examples 7d–7g. Expression of the desired genetic construction in appropriate *C. crescentus* strains may be done using the procedures outlined in part A(3) of this example.

(3) Alternate PCR Procedures: may be used to prepare a heterologous segment for direct insertion into the BamHI site with the deletion versions of the rsaA gene. The procedure is essentially the same as described in part B(1) of this example.

EXAMPLE 7

Transfer to a Native S-layer Gene Chromosomal Site as a Single Crossover Event

Fusion of a carrier cassette containing heterologous DNA segments to a C-terminal S-layer protein segment plasmid results in a plasmid that is not maintained in *Caulobacter*. Selection for the antibiotic marker on the plasmid results in detection of the rescue events. Most commonly these are single crossover homologous recombination events. The result is a direct insertion of the entire plasmid into the chromosome. Thus the resident copy of the S-layer gene remains unchanged as well as the incoming modified S-layer gene. In such cases it may be desirable to use *Caulobacter* strains in which the resident S-layer gene has been inactivated by adapting known procedures. One example is *C. crescentus* strain CB15AKSac which has an antibiotic resistance gene cassette introduced at a position in the S-layer gene about 25% of the way from the 5' terminus.

EXAMPLE 8

Transfer to a Native S-layer Gene Chromosomal Site as a Double Crossover Event In certain cases it may be desirable to completely exchange a resident S-layer gene with an incoming modified version. One method is by the incorporation of a sacB gene cassette (Hynes, M. F., et al., (1989) Gene 78: 111–119) into pUC8 based plasmids carrying the desired chimeric gene construction. This cassette contains a levansucrase gene from *Bacillus subtilis* that, in the presence of sucrose, is thought to produce a sugar polymer that is toxic to most bacteria. One first selects for a single crossover event as described in Example 7. Subsequent growth on sucrose-containing medium results in the death of all cells except those that lose the offending sacB gene by homologous recombination within adjacent gene copies. Two events are possible; restoration of the resident copy of the S-layer gene or replacement of the resident copy with the incoming modified gene. A screen with insertion DNA as probe or antibody specific to the heterologous gene product identifies successful gene replacement events. The method requires that S-layer gene sequence or native sequences immediately adjacent to an S-layer gene be present on both sides of the heterologous sequence and is best suited for deletion versions of a S-layer gene.

Other methods are available for the delivery of genes to the chromosome of *Caulobacter*. Methods involving the use of the transposons Tn5 and Tn7 as a means of delivery of genes to random chromosome locations are available (see: Barry, G. F. (1988) Gene 71:75–84.). The use of the xylose utilization operon as a target for chromosome insertion have also been described. This method involves the incorporation of a portion the operon into a pUC8 based plasmid construction. This allows homologous recombination within the xylose operon as a means of plasmid rescue. Loss of the ability to use xylose as a nutrition source confirms the rescue event.

EXAMPLE 9

Transformation and Expression of Heterologous Protein in *Caulobacter* Other Than *C. crescentus*

Using the procedures described above, a DNA construct made according to Examples 4 and 6 was introduced into the freshwater S-layer producing *Caulobacter* identified as FWC42 in MacRae, J. D. and J. Smit (1991) and in Walker, S. G. et al. (1992). FWC42 is clearly distinct as a species separate from *C. crescentus*. The construct contained 3 copies of the pilus epitope and a nucleotide sequence encoding amino acids 690–1026 of RsaA as the secretion signal. The heterologous polypeptide was expressed by the transformed FWC42 cells and was secreted at sufficient levels such that the secreted protein was found in the cell medium as an aggregate.

EXAMPLE 10

Demonstration of Type I Secretion Mechanism and Sequence Similarity in Different *Caulobacter* Species The following non-*C. crescentus* species of freshwater *Caulobacter* as described in MacRae, J. D. and J. Smit (1991) and in Walker, S. G. et al. (1992) were employed in this Example: FWC1, FWC8, FWC9, FWC17 and FWC19, FWC28, FWC32, FWC39 and FWC42.

Employing the materials and methods described in Awram, P. and J. Smit (1998) J. of Bacteriology 180:3062–3069, species FWC8, 9, 17, 19, 28, 32, 39 and 42 were transfected with plasmids containing the *P. aeruginosa* alkaline protease gene (aprA) which is a known type I secretory protein. The protease was shown to be secreted at levels comparable to the levels of such protease reported by Awran and Smit for *C. crescentus* transformed in the same way. Thus, the transport mechanism in the non-*C. crescentus* species are Type I mechanisms capable of recognizing diverse Type I (C-terminal) secretion signals.

The following recombinant DNA and DNA sequencing methods are described in Awram, P. and J. Smit (1998) and may be used with appropriate adaptation in this invention. These procedures may be used in screening suitable *Caulobacter* for use as host organisms and for identification of *Caulobacter* of this invention. *E. coli* DH5$_\alpha$ (Life Technologies) was used for all *E. coli* cloning manipulations. *E. coli* was grown at 37° C. in Luria broth (1% tryptone, 0.5% NaCl, 0.5% yeast extract) with 1.2% agar for plates. *Caulobacter* was grown at 30° C. in PYE medium (0.2% peptone, 0.1% yeast extract, 0.01% CaCl$_2$, 0.02% MgSO$_4$) with 1.2% agar for plates. Ampicillin was used at 100 μg/ml, streptomycin was used at 50 μg/ml, kanamycin was used at 50 μg/ml, and tetracycline was used at 0.5 μg/ml for *Caulobacter* and at 10 μg/ml for *E. coli* when appropriate.

Standard methods of DNA manipulation and isolation were used. Electroporation of *Caulobacter* was performed as described above. Southern blot hybridizations were done in accordance with the membrane manufacturer's manual (Amersham Hybond-N). Radiolabelled probes were made by nick translation using standard procedures.

PCR product containing rsaD and rsaE was generated using primers 5'-CGGAATCGCGCTACGCGCTGG-3' (SEQ ID NO:2) and 5'-GGGAGCTCGAAGGGTCCTGA-3' (SEQ ID NO:3). Product was generated using Taq polymerase (Bethesda Research Laboratories) and following the manufacrure's suggested protocols. Following a 5-min denaturation at 95° C., two cycles of 1 min at 42° C., 2 min at 65° C. and 30 s at 95° C. were followed by 25 cycles of 1 min at 55° C., 2 min at 65° C., and 30 s at 95° C. The vector pBSKS+Stratagene was cut at the EcoRV site and T tailed. The PCR product was ligated into this vector so that rsaD and rsaE would be in the same orientation as the lacZ promoter of pBSKS+. This construct was called pRAT5.

Plasmid pBBR5 was constructed from plasmids pBBRIMCS (Kovach, M. E. et al. (1994) BioTechniques 16:800–802) and pHP45Ω-Tc (Fellay, R. et al. (1987) Gene 52:147–154). The Ω-Tc fragment from pHP45Ω-Tc was removed by using HindIII, and the ends were blunted by using T4 polymerase. A 0.3-kbp portion of the CMr-encoding gene was removed from pBBRIMCS b7 cutting with DraI and replaced with the blunted Ω-Tc Fragment, producing a Tcr broad-host-range vector that replicates in *Caulobacter*.

Plasmid pRAT4ΔH was made by removing the ClaI-HindIII fragment from pTZ18UB:rsaAP (Bingle, W. H. et al. (1997) J. Bacteriol. 179:601–611) and replacing it with the ClaI-HindIII fragment from pRAT1 containing the C-terminus of rsaA and the complete rsaD and rsaE genes.

A NA1000 cosmid library (Alley, M. R. et al. (1991) Genetics 129:333–341) was probed with radiolabelled rsaA.

11 cosmid clones hybridizing to the probe were isolated. Southern blot analysis was used to determine which cosmids contained DNA 3' of rsaA. An 11.7 kb Sst1-EcOR1 fragment containing rsaA plus 7.3 kb of 3' DNA was isolated from one of the cosmids and cloned into the Sst1-EcoR1 site of pBSKS+; the resulting plasmid was named pRAT1. The 3' end of the cloned fragment consisted of 15 bp of pLAFR5 DNA containing Sau3A1, SmaI; and EcoRI sites.

BamHI fragments from pRAT1 were subcloned into the BamHI site of vector pTZ18R for sequencing. The 3'-end fragment was subcloned into pTZ18R by using BamHI and EcoRI. The 5'-end fragment was subcloned into pTZ18R by using HindIII. Sequencing was performed on a DNA sequencer (Applied Biosystems™ model 373). After use of universal primers, additional sequence was obtained by "walking along" the DNA using 15-bp primers base on the acquired sequence. Nucleotide and amino acid sequence data were analyzed by using Geneworks™ and MacVector™ software (Oxford Molecular Group) or the National Center for Biotechnology Information BLAST e-mail server using the BLAST algorithm. Protein alignments were generated by using the ClustalW™ algorithm as implemented by the MacVector™ software and using the default settings.

Sequences for rsaD and rsaE have been assigned GenBank Accession No. AF062345. The proteins have the following sequences:

RsaD (SEQ ID NO:4):
MFKRSGAKPTIFDQAVLVARPAVITAMVFSFFI-
NILAVSPLYMLQVYDRVLTSRNVSTLIVLTVICVFL
FLVYGLLEALRTQVLVRGGLKFDGVARDPIFKSV-
LDSTLSRXGIGGQAFRDMDQVREFMTGGLIAFCKAP
WTPVFVIVSWMLHPFFGILAIIACIIIFGLAVMND-
NATKNPIQMATMASIAAQNDAGSTLRNAEVMKAMG
MWGGLQARWRARRDEQVAWQAAASDAGGAVMSG-
IKVFRNIVQTLILGGGAYLAIDGKISAGMIAGSILV
GRALAPIEGAVGQWKNYIGARGAWDRLQTML-
REEKSADDHMPLPEPRGVLSAEAAILPPGAQQP-
TMRQA SFRIDAGAAVALVGPSAAGKSSLLRGIVG-
VWPCAAGVIRLDGYDIKQWDPEKLGRHVGY-
LPQDIELFSGT VAQNLARFTEFESQEVIEAATLAGVH-
EMIQSLPMGYDTAIGEGGASLSGGQRQRLALARAV-
FRMPALLVL DEPNASLDQVGEVALMEAMKRLKAA-
KRTVIFATHKVNLLAQADYIMVINQGVISK- FGER-
DRCWPS

RsaE (SEQ ID NO:5):
MKPPKIQRPTDNFQAVARIGYGIIALTFVGLLGWA-
AFAPLDSAVIANGVVSAEVSQDVQHLEGGMLAKIL
VREGEKVKAGQVLFELDPTQANAAAGITRNQY-
VALKAMEARLLAERDQRPSISFPADLTSQRADPM-
VARA IADEQAQFTERRQTIQGQVKLMNAQR-
LQYQSEIEGIDRQTQGLKDQLGFIEDELIDLRKL-
YDKGLVPRPR LLALEARAGSLSGSIGRLTA-
DRSKAVQGASDTQLKVRQIKQEFFEQVSQSIT-
ETRVRLAEVTEKEVVASD AQKRIKIVSPVNGTAQNL-
RFFTEG AVVRAAEPLVKIAPEDEAFVIQAHFQPTDV-
DNVHMGMVTEVRLPAE HSAGNPDPERHDPVAV-
ADRISDPQKQARLFLGIVRVDKQLPPHLRGRVT-
AGMPAQVIVPTGERTVLQYL FSPLRDTLRTTMREE

The Table below sets out results of initial sequencing of S-layer related genes in 2 strains of C. crescentus (NA1000 and CB2) and four non-C. crescentus species of S-layer producing freshwater Caulobacter (FWC6, 8, 19, 27 and 39). Genes identified as A, D and E are the S-layer structural gene, the ABC transporter gene and the membrane fusion protein (MPF) respectively. In the C. crescentus strains, the latter genes are rsaA, rsaD, and rsaE, respectively. The transport protein cents are highly conserved within and among the species. Within the C. crescentus species, there is high conservation of the rsaA gene, including the C-terminal secretion signal. A region of the S-layer gene in FWC27 outside the secretion signal region shows clear divergence from the equivalent region in the two C. crescentus strains.

Further sequencing studies comparing the S-layer protein gene (A), the ABC-transporter gene (D) and the MFP gene (E) of FWC1, 9, 19, 39 and 42 to the rsaA, rsaD and rsaE genes of C. crescentus strain CB15A produced the following results. FWC1 and FWC19 respectively exhibited about 32% and about 27% identity over the last 300 C-terminal amino acids of the A gene, as compared to rsaA. For the last 100 C-terminal amino acids, identity of FWC1 and FWC19 sequences to rsaA was about 50% and 41% (respectively), with the most significant identity being in the last 62 amino acids. Sequencing of various 35 to about 350 amino acid segments of the D gene from FWC1, FWC9, FWC19, FWC39 and FWC42 resulted in sequence identity to rsaD of at least about 79%. Sequencing of large portions of the E gene from FWC19 and FWC42 (about 368 and about 290 amino acids respectively) demonstrated about 85% and about 73% identity (respectively) to the rsaE gene.

Approximately the last 100 C-terminal amino acids of the A gene for FWC1 (SEQ ID NO:6) and FWC19 (SEQ ID NO:7) are set out below.

FWC1
TTDTLKFANTG-TETFSTKVDLTGVNDFTAALN-
AAAAGNGGGNGII TWFQYGGNTYIVEDRD-
AGNTFNVATDIVVKLTGAVDLST-AVLSAFGRRS
SLTLV

FWC19
RAHMILKRHVSDRWGRHVARLVQLPGRPCPKLSD-
AATTGNASHKV SWFVYGGDTYLVYLVKMST-
LAPPSKTARTIVV TGTTNDLTK-ATFDGAAH TLTLG

This invention now being described, it will be apparent to one of ordinary skill in the art that changes and modifications can be made thereto without departing from the spirit or scope of the appended claims.

| | | A | | D | | E | |
|---|---|---|---|---|---|---|---|
| FWC species | Size of A | Identity[1] | Similarity[2] | Identity[1] | Similarity[2] | Identity[1] | Similarity[2] |
| NA 1000 | 98 kDa | 100% 1026/1026 | 100% 1026/1026 | 100% 555/555 | 100% 555/555 | 100% 435/435 | 100% 435/435 |
| CB2 | 98 kDa | 100% 1026/1026 | 100% 1026/1026 | 99.8% 554/555 | 99.8% 554/555 | 99.3% 432/435 | 99.3% 432/435 |
| FWC 6 | 181 kDa | ND | ND | 85% 381/451 | 92% 415/451 | ND | ND |
| FWC 8 | 122 kDa | ND | ND | 86% 390/451 | 94% 424/451 | ND | ND |

|             |           | A                    |                       | D                    |                       | E                    |                       |
|-------------|-----------|----------------------|-----------------------|----------------------|-----------------------|----------------------|-----------------------|
| FWC species | Size of A | Identity[1]          | Similarity[2]         | Identity[1]          | Similarity[2]         | Identity[1]          | Similarity[2]         |
| FWC 19      | 108 kDa   | ND                   | ND                    | 85% 357/419          | 93% 390/419           | 82% 355/435          | 88% 381/435           |
| FWC 27      | 145 kDa   | 29% 57/198           | 40% 80/198            | ND                   | ND                    | ND                   | ND                    |
| FWC 39      | 193 kDa   | ND                   | ND                    | 84% 380/451          | 92% 416/451           | ND                   | ND                    |

[1]Identical amino acids to NA 1000/number of amino acids predicted by sequence
[2]Identical and similar amino acids to NA 1000/number of amino acids predicted by sequence
ND Not Determined
Amounts of sequence obtained

| | | |
|---|---|---|
| A | CB2    | amino acids 1–1026 (100% of sequence) |
|   | FWC 27 | amino acids 38–250 |
| D | CB2    | amino acids 1–555 (100% of sequence) |
|   | FWC 6  | amino acids 45–495 (81%) |
|   | FWC 8  | amino acids 45–495 (81%) |
|   | FWC 19 | amino acids 80–495 (75%) |
|   | FWC 39 | amino acids 45–495 (81%) |
| E | CB2    | amino acids 1–435 (100% of sequence) |
|   | FWC 19 | amino acids 1–435 (100%) |

I claim:

1. A host cell for expression and secretion of a heterologous polypeptide, wherein the cell is a *Caulobacter* comprising at least one surface layer transport protein having an amino acid sequence sharing at least 80% sequence identity with SEQ ID NO:5, and wherein the host further comprises a DNA construct comprising DNA encoding a polypeptide heterologous to a surface layer protein of the cell 5' from and operably linked to DNA encoding a *Caulobacter* surface layer protein secretion signal, with the proviso that when the cell comprises transport proteins having the same sequence as both SEQ ID NO:4 and SEQ ID NO:5, the secretion signal is not from *C. crescentus*.

2. The cell of claim 1 wherein at least one of the transport proteins of the cell has an amino acid sequence the same as SEQ ID NO:5.

3. The cell of claim 2 having transport proteins with the same amino acid sequence as SEQ ID NO:5, and wherein the secretion signal does not comprise SEQ ID NO:1.

4. The cell of claim 1 wherein the DNA construct further comprises an operably linked promoter recognized by the cell.

5. A method for identifying a *Caulobacter* suitable for use as a host cell for expression and secretion of a heterologous polypeptide comprising:
   (a) extracting DNA from a candidate non-*C. crescentus* Caulobacter;
   (b) contacting the DNA with an oligonucleotide capable of selective hybridization to a nucleotide sequence encoding SEQ ID NO:5; and
   (c) determining whether the oligonucleotide hybridizes to the DNA.

6. The method of claim 5 wherein the oligonucleotide is labelled and said determining is by detection of the presence of the label bound to the DNA.

7. The method of claim 5 wherein said determining is by amplification of DNA with the oligonucleotide as a primer, followed by detection of an amplification product.

8. A DNA construct comprising one or more restriction sites for facilitating insertion of DNA into the construct, wherein the construct further comprises DNA encoding a surface layer protein secretion signal of a non-*C. crescentus* Caulobacter, wherein said non-*C. crescentus* Caulobacter comprises at least one surface layer transport protein comprising an amino acid sequence sharing at least 80% sequence identity with SEQ ID NO:5.

9. A DNA construct comprising DNA encoding a polypeptide not present in *Caulobacter* surface layer protein, 5' from and operatively linked to DNA encoding a surface layer protein secretion signal of a non-*C. crescentus* Caulobacter, wherein said non-*C. crescentus* Caulobacter comprises at least one surface layer transport protein comprising an amino acid sequence sharing at least 80% sequence identity with SEQ ID NO:5.

10. The DNA construct of claim 9 further comprising an operably linked promoter recognized by *Caulobacter*.

11. The DNA construct of claim 8 wherein the secretion signal has an amino acid sequence which does not comprise SEQ ID NO: 1.

12. A bacterial cell comprising a DNA construct of claim 9.

13. The cell of claim 12, wherein the cell is a *Caulobacter*.

14. The cell of claim 12, wherein the cell is a *C. crescentus*.

15. The cell of claim 13 wherein the DNA construct further comprises an operably linked promoter recognized by *Caulobacter* wherein the DNA construct is expressed in the cell and the protein is expressed is secreted by the cell.

16. The cell of claim 2 wherein the DNA construct further comprises an operably linked promoter recognized by the cell.

17. The cell of claim 3 wherein the DNA construct further comprises an operably linked promoter recognized by the cell.

18. The DNA construct of claim 9 wherein the secretion signal has an amino acid sequence which does not comprise SEQ ID NO:1.

19. The DNA construct of claim 10 wherein the secretion signal has an amino acid sequence which does not comprise SEQ ID NO:1.

20. A method for identifying a non-*C. crescentus Caulobacter* suitable for use as a host cell for expression and secretion of a heterologous polypeptide comprising:

(a) selecting a candidate non-*C. crescentus Caulobacter*; and (b) determining whether the candidate has a gene product sharing at least 80% sequence identity with SEQ ID NO:5.

* * * * *